United States Patent
Karamavuş et al.

(10) Patent No.: US 10,393,652 B2
(45) Date of Patent: Aug. 27, 2019

(54) PORTABLE OPTICAL APPARATUS FOR DIFFUSE REFLECTANCE SPECTROSCOPY

(71) Applicant: TUBITAK, Ankara (TR)

(72) Inventors: Yunus Karamavuş, Kocaeli (TR); Hasan Basri Çelebi, Kocaeli (TR); Yildiz Uludağ, Kocaeli (TR); Gökhan Bektaş, Kocaeli (TR); Veysi Cansu, Kocaeli (TR); Dadaş Riza, Kocaeli (TR)

(73) Assignee: TUBITAK, Ankara (TR)

( * ) Notice: Subject to any disclaimer, the term of this patent is extended or adjusted under 35 U.S.C. 154(b) by 0 days.

(21) Appl. No.: 16/073,331

(22) PCT Filed: Jan. 1, 2016

(86) PCT No.: PCT/IB2016/050375
§ 371 (c)(1),
(2) Date: Jul. 26, 2018

(87) PCT Pub. No.: WO2017/130020
PCT Pub. Date: Aug. 3, 2017

(65) Prior Publication Data
US 2019/0041328 A1 Feb. 7, 2019

(51) Int. Cl.
G01N 21/47 (2006.01)
A61B 5/00 (2006.01)
G01J 3/02 (2006.01)

(52) U.S. Cl.
CPC ......... G01N 21/474 (2013.01); A61B 5/0075 (2013.01); A61B 5/441 (2013.01);
(Continued)

(58) Field of Classification Search
CPC ......... G01N 21/474; G01N 2021/4742; G01N 2021/4752; G01N 2021/4759; A61B 5/0075; A61B 5/441; G01J 3/02
See application file for complete search history.

(56) References Cited

U.S. PATENT DOCUMENTS 4,223,680 A * 9/1980 Jobsis ................. A61B 5/0059
600/324
8,169,470 B2 * 5/2012 Ishihara ............. A61B 1/00009
348/68
(Continued)

FOREIGN PATENT DOCUMENTS

GB 2115175 A 9/1983

OTHER PUBLICATIONS

Zonios, G., & Dimou, A. Modeling diffuse reflectance from semi-infiniteturbidmedia:applicaiton to the study of skin optical properties. Optix Express, Sep. 18, 2006.
(Continued)

Primary Examiner — Dominic J Bologna
(74) Attorney, Agent, or Firm — Gokalp Bayramoglu

(57) ABSTRACT

An optical apparatus for obtaining a reflectance spectrum includes a first means for generating a light, a second means for transferring and receiving the light on a substrate, a third means for collecting a diffusely reflected light, and a fourth means for separating the diffusely reflected light from a specular reflected light to obtain information about a concentration of a chromophore in the substrate. The second means is an optic probe made of Poly(methyl methacrylate) (PMMA) material including an inner rod and an outer rod, the inner rod is nested within the outer rod for collection and for illumination, the inner rod and the outer rod are coaxial, the inner rod is longer than the outer rod, the inner rod is isolated from the outer rod with a semi mirrored isolator, the reflected light is reflected from deep within the substrate by the inner rod.

7 Claims, 3 Drawing Sheets

(52) U.S. Cl.
CPC ........ *G01J 3/02* (2013.01); *G01N 2021/4742* (2013.01); *G01N 2021/4752* (2013.01); *G01N 2021/4759* (2013.01)

(56) References Cited

U.S. PATENT DOCUMENTS

| | | | |
|---|---|---|---|
| 2002/0084417 A1* | 7/2002 | Khalil | A61B 5/14532 250/341.8 |
| 2007/0265513 A1* | 11/2007 | Schenkman | A61B 5/0059 600/363 |
| 2009/0022463 A1 | 1/2009 | Bouma et al. | |
| 2015/0015888 A1* | 1/2015 | Gulati | G01J 3/42 356/446 |

OTHER PUBLICATIONS

Nicholes, M. G. et al. Design and testing of a white-light, steady-state diffuse reflectance spectrometer for determination of optical properties of highly scattering system. Appl. Optics, Jan. 1, 1997, 36 (1), 93-104.

Bosschaart, N. et al. Optical properties of neonatal skin measured in vivo as a function of age and skin pigmentation, Journal of Biomedical Optics, Sep. 2011,vol. 16(9).

Bhadri, P. R. Spectrometric Quantificaiton of Bilirubin in Hemorrhagic Spinal Fluid using an Innovative Algorith,. Medicinal Chemistry, 2007, 3, 21-27.

Saidi, Iyad. Salam. Transcutaneous Optical measurement of hyperbilirubinemia in neonates, Rice University, 1992.

* cited by examiner

PORTABLE OPTICAL APPARATUS FOR DIFFUSE REFLECTANCE SPECTROSCOPY

CROSS REFERENCE TO RELATED APPLICATIONS

This application is the national phase entry of International Application No. PCT/IB2016/050375, filed on Jan. 26, 2016, the entire contents of which are incorporated herein by reference.

TECHNICAL FIELD

The present invention relates to a new optical apparatus for portable diffuse reflectance spectroscopy; and more particularly, relates to a novel optical probe design that is made of Poly(methyl methacrylate) (PMMA) material for the spectroscopic measurement or analysis of biological attributes of tissue.

BACKGROUND

Obtaining optical properties of skin leads to useful information about the skin physiology, morphology, and composition. These can be obtained in a non-invasive manner and in real time using an optical method of analysis. One such optical method is reflectance spectroscopy consists of two components: specular reflectance and diffuse reflectance. The specular reflectance of a skin sample is the light which does not propagate into the sample, but rather reflects from the front surface of the sample. This component contains information about the biological sample at the surface. In order to gather information from the deeper section of the biological tissues, diffuse reflectance spectroscopy can be applied.

Diffuse reflectance spectra are obtained from the light that has traveled within the tissue. As the beam penetrates the biological tissue, the direction of propagation changes randomly due to the refractive index variations in the layers beneath. The light is attenuated on its pathway due to the absorption and scattering events. After numerous scattering events, some of the light emerges from the surface. The intensity of this reflected light carries information regarding the absorption and scattering of light through the medium which can be correlated with the morphology to determine the pathological state of the tissue and/or the concentration of a biochemical/analyte in the tissue. Diffuse Reflectance Spectroscopy has been widely used for non-invasive analysis and the characterization of the biological tissues. This technique provides rapid quantitative measurements of pigments within the tissue. Non-invasive measurements via reflectance spectroscopy are desirable because they are painless, do not require fluid drawn from the body, carries little risk of contamination or infection, and do not generate any hazardous waste and enables rapid measurement. Accurate, non-invasive determination of bilirubin, as an example, could reduce many of the complications associated with the newborn jaundice. Similarly, accurate, non-invasive determination of various disease states could allow faster, more convenient screening and diagnosis, allowing more effective treatment. Biomedical applications of reflectance spectroscopy include study on colon, esophagus, stomach, bladder, cervix, ovaries, breast, brain, liver, pancreas, heart, oral tissues, and skin.

A typical measurement setup for reflectance spectroscopy consists of a light source for illumination of skin, a detector for evaluation of reflected light, and an optical probe for delivery and collection of the reflected light. A light source can be a halogen lamb a tungsten lamb, a light emitting diode (LED) etc. A detector can be a photo detector or a spectrometer. Generally, fiber optic cables are being used as an optic probe for light transmission. Optic probes consist of two separate light paths, one for the delivery of light to the targeted biological tissue and one for the collection of light coming from the targeted biological tissue.

SUMMARY

Technical Problem

Designing of a portable diffuse reflectance spectroscopy is a challenge due to the difficulties faced to miniaturize the device and the manufacturing of the optical apparatus, which leads to a high cost. Furthermore, collecting the returning light from deep within the tissue is challenging due to the specular component of the reflected light. Longer integration time is another problem of reflectance spectroscopy.

Traditionally, the accessory used to measure diffuse reflectance is an integrating sphere. Because of the geometry of the integrating sphere, it has the ability to collect most of the reflected light, it can remove any directional preferences, and present an integrated signal to the detector. However, for a portable skin measuring device, application of diffuse reflectance spectroscopy necessitates being compact, lightweight, small sized and user friendly optical apparatus. Integrating sphere structure does not allow miniaturization and hence not suitable to be used in a portable device.

Currently, fiber optic probes with varying diameters and fiber cable arrangements are in use for the optical probes. For example, a construction of a probe with a linear alignment of fibers, and placing the detection fibers in different places is a design currently in use. An alternative design is, a circular fiber arrangement with a source fiber in the middle of all other fibers. Also, it is possible to face a micro machined fiber optical sensor with different number of source fibers and numerous collection fibers. The source fibers are placed obliquely with the angle 45°. In another fiber optic probe, 5 fibers are used which are cast in-line in an aluminum probe. The first fiber is used for the illumination and others are used for the source detection (source-detector distances are 0.6 mm, 1.2 mm, 1.8 mm, and 2.4 mm). Despite the wide use of fiber optic probes, their manufacturing process is rather complex. Especially, while designing a custom designed probe, one can need to cut the fibers which are not an easy process. Cutting the fibers needs special cutter devices and after the cutting process fibers' endings need to be polished which is another difficult and time consuming process. Furthermore, arranging fibers in a desired alignment as making fiber bundle, is not easy because of small diameters. Another important drawback of using fiber is the dead area between fibers in a fiber bundle. This dead area is unfavorable because of not allowing light transportation.

The main components of the reflected light include specular reflectance and diffuse reflectance. The diffuse component of the reflected light is desirable, and even essential, if the reflectance spectroscopy is used for examining the subcutaneous tissue, since specular reflectance component only contains information about the surface of the skin. The information about the presence or concentration of a chromophore in the subcutaneous tissue, such as hemoglobin and bilirubin, is carried by diffusely reflected light from the human tissue. The epidermis layer has very little or no blood and thus corresponding diffusely reflected light component from epidermis layer has little or no information about the biological information. Consequently, it is critical to collect only diffusely reflected light returning from the subcutaneous tissue.

Diffuse reflectance spectrum carries the information about the concentration of the biological chromophores deep inside the human skin. It is critical to acquire the sufficient reflected light intensity to calculate the concentration of those chromophores. In order to have this sufficient intensity, integration time or efficiency of the system can be increased. However, in some applications, such as transcutaneous bilirubinometry, fast integration time is required to decrease the environmental noise effects such as motion blur. Thus, achieving shorter integration time is one of the most vital issues in diffuse reflectance spectroscopy. Increasing the light transmission efficiency is a mean to shorten the integration time. For better light transmission efficiency, light delivery path should be coupled to the light source effectively and so should light collection path with detector.

Technical Solution

The present invention comprises a new optical probe design for diffuse reflectance spectroscopy measurements; more particularly, a novel optical apparatus design in which an optical probe made of Poly(methyl methacrylate) (PMMA) is used to transfer and receive light for the spectroscopic measurements. Here, a novel device is presented with a new optical apparatus that provides smaller size, easy manufacturing process and lower cost. Also, optical apparatus is designed in such a way that only diffusely reflected light can be collected by the detector. Shorter integration time is another superiority of this novel optical apparatus.

While designing a portable diffuse reflectance spectroscopy instrument, a compact, lightweight, small sized and user friendly design should be taken into account. Obtaining such an optical apparatus, using PMMA rods for light transmission is a solid solution. Besides using PMMA material in the designed optical probe, the present invention has novelty in optical apparatus components (detector, source, and probe) placement. A micro spectrometer is used as a detector and placed on top of the optical apparatus coupling to the light collection path. Below the spectrometer, light source is placed that is coupled to the light delivery path. This placement creates a compact structure for the designed optical apparatus.

Using PMMA material in the optical probe has several advantages. First of all, it enables an easy manufacturing process compared to fiber optic cable based systems. Also, PMMA optical probe does not need advanced cleaving devices, polishing materials or a bundling process as required by optical fiber cables. Only one piece of a PMMA rod with couple of mm core size has capability to carry sufficient light intensity to either transfer or collect light. Eventually, PMMA probe is much easier to manufacture, more compact and more affordable than the conventional optical fiber probes. These attributes results in a superior optical probe for any spectroscopic analysis.

Another important aspect of this novel optical apparatus is, it provides maximum light transmission efficiency by minimizing the dead zone. The present invention provides an optical probe consisted of two nested PMMA rods with 4 mm and 8 mm core sizes. The outer rod is used to expose the skin surface with a white light produced by a LED. And the reflected light emerging from the various layers of the tissue is collected by the inner rod, which is coupled to a spectrometer. Because of the tightly nested structure of two cylindrical PMMA rods, there is no dead zones as seen in fiber optic cable bundles.

The proposed optical apparatus includes a pressure-sensitive probe that is activated when pressed on human skin. This illuminates the skin with a bright strobe light generated by a LED light source. This bright light travels for a short distance through the skin where the pressure-sensitive probe is applied and brightens the underlying subcutaneous tissue. The scattered light is then channeled through the inner PMMA rod that is isolated from the outer PMMA rod. The specular component of the reflectance spectrum cannot follow the inner path because of this isolation between the two rods. Thus, only diffusely reflected light reaches the spectrometer module.

Shorter integration time is another advantage of the proposed optical apparatus. Higher light transmission efficiency is the main reason of achieving shorter integration time. Although, the attenuation coefficient of PMMA material is not smaller than the fiber optic cable, the dissipation is negligible because of the short illumination channels. In addition, because of the larger contact area of the probe to the skin surface, higher light intensity is received than the fiber optic cable can permit.

With these and other solutions in view, which will become apparent to one who is expert in the art, this invention resides in the novel construction, original placement of components, and increased light transmission efficiency of optical apparatus for diffuse reflectance spectroscopy. More particularly a new approach is offered by the use of PMMA material in the optical probe design that makes this invention novel.

Advantageous Effects

This invention is advantageous because it is compact, lightweight, small sized and user friendly.

Another advantage of this invention is to provide a novel placement of detector, source, and optic probe.

It is another advantage of this invention is to use a white LED with a flat spectrum in visible range.

It is yet another advantage of this invention is, use of PMMA material in the optical probe design. Using this material makes this invention manufacturing process easy and affordable.

It is another advantage of this invention is the minimization of dead zone that prevents the light transmission.

It is still another advantage of this invention is to provide maximum light transmission efficiency.

It is still another advantage of this invention is to provide shorter integration time.

It is still another advantage of this invention is to provide a pressure-sensitive probe, which is invoked when pressed on the human skin.

It is still another advantage of this invention is that it provides collection of diffusely reflected light.

BRIEF DESCRIPTION OF THE DRAWINGS

The accompanying drawings illustrate a complete embodiment of the invention according to the best mode so far devised for the practical application of the principles thereof, and in which.

DETAILED DESCRIPTION

Figure 1:
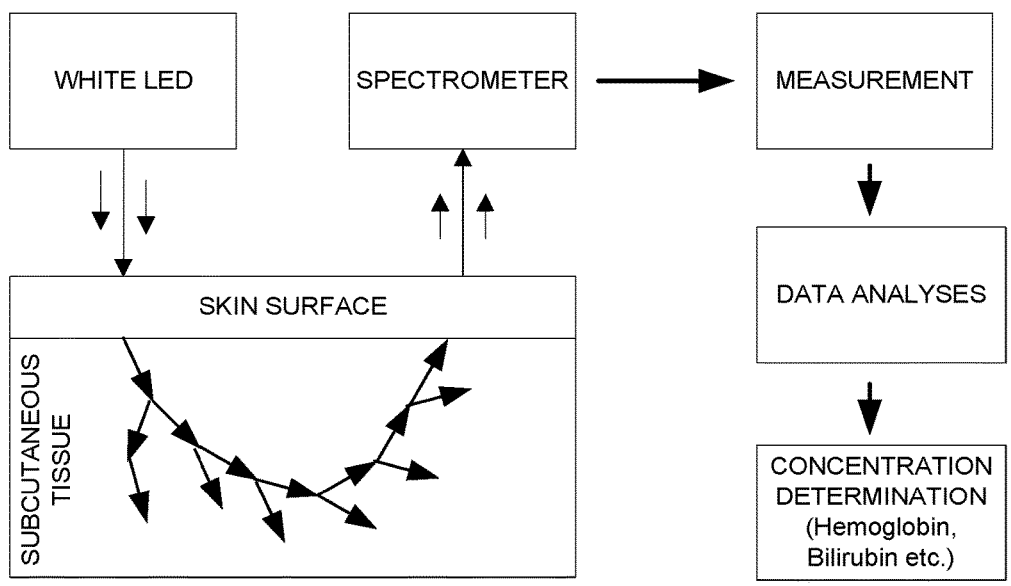
FIG. 1 is a schematic and block diagram of the diffuse reflectance measurement system

In FIG. 1, it is shown that the light that is produced by a white LED is directed to the skin surface. The light penetrates into the skin tissue by randomized propagation. After numerous scattering events, some of the light emerges from the skin surface. This reflected light is collected by a spectrometer to obtain the reflectance spectra. From this spectra, it is possible to determine the concentration of the target chromophore in the subcutaneous tissue by the appropriate data analyses.

Figure 2:
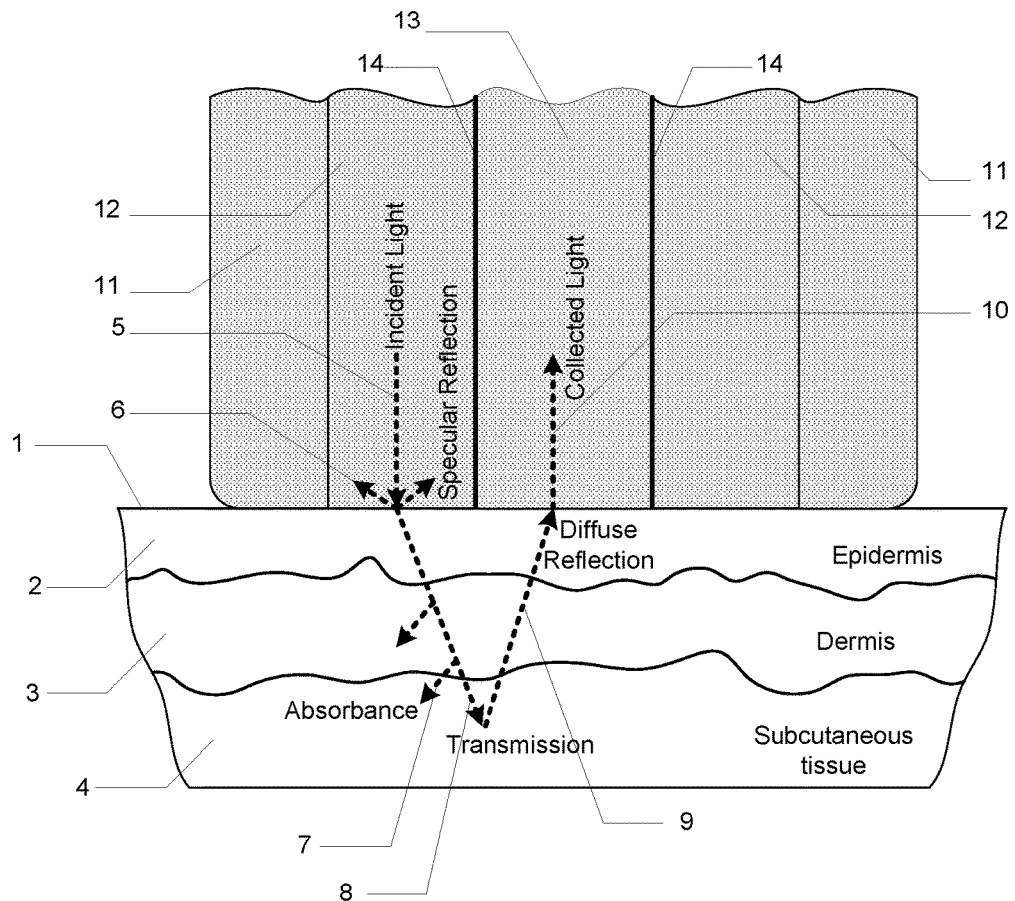
FIG. 2 is a schematic representation of the incident light on a skin tissue

FIG. 2 illustrates the skin surface 1 illumination by an incident light coming from the outer PMMA rod 12. As depicted in the simplified representation, the skin includes three layers, the upper layer or epidermis 2, a middle layer or dermis 3, and subcutaneous tissue 4. Incident light 5 illuminates the skin surface and penetrates into the subcutaneous tissue. A portion of the light energy may be reflected specularly 6 which cannot not reach the light collection path. Instead, a tissue sample may absorb a portion of the light energy, resulting in absorbed light energy 7. A third phenomena includes transmitted energy 8 into the deeper tissue. Lastly, a portion of the light can be diffusely reflected 9. As shown in FIG. 1 diffusely reflected portion of light ray change the direction several times and then this portion 10 is collected by the inner PMMA rod 13. To prevent the light transmission from one rod to the other, the rods are isolated from each other by a semi mirrored isolator 14. In this way only diffusely reflected light is analyzed. Also, the semi-mirrored isolator increases the light transmission efficiency. The outer isolation is provided by the optical probe holder 11, which holds the other components of the optical apparatus.

Figure 3:
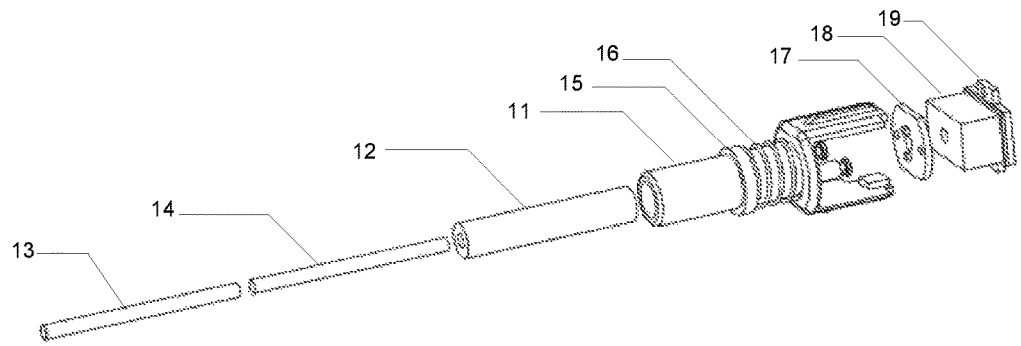
FIG. 3 shows the expanded figure of optical apparatus

The expanded schematic view of the optical apparatus is shown in FIG. 3. Two cylindrical PMMA rods 12, 13 are placed in a nested structure and isolated from each other with an isolator material 14. Optic probe holder 11 contains a spring 16 with a spring holder 15 allowing pressure-sensitive activation mechanism. This mechanism allows the appropriate pressure on the skin surface, and thus helps providing correct measurement results. Illumination of the target skin surface is achieved by the LEDs, placed on the LED circuit card 17. After a sufficient illumination of the skin, the diffusely reflected light that is typically reflected by various depths within the tissue is collected by the inner PMMA rod and carried to the spectrometer 18. This spectrometer is placed on a circuit card 19.

Figure 4:
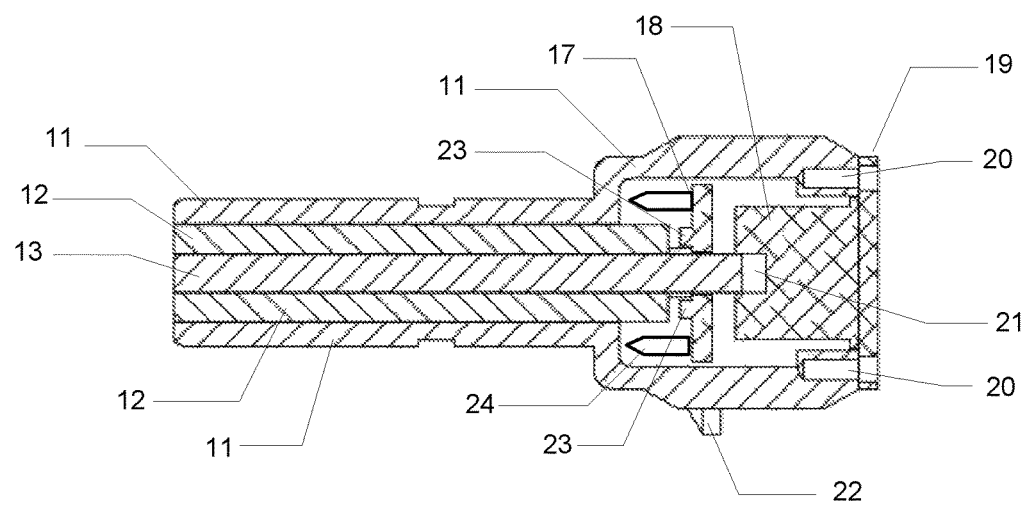
FIG. 4 shows the cross sectional view of optical apparatus

Referring now to FIG. 4, there is shown a cross sectional view of optical apparatus. In FIG. 4 the placement of the optical apparatus components is seen. From the top side to the bottom, spectrometer circuit card 19 is in the first place that is fixed with two screws 20. The collected light enters the spectrometer 18 through its slit 21. Collection PMMA rod 13 is directly coupled to this slit. Below the spectrometer, LED circuit card 17 is placed and fixed by two screws 24. On this card, there are two white LEDs 23 with wide flat spectrums (for example from 350 nm to 750 nm wavelengths). These LEDs are positioned adjacent the top surface of the source PMMA rod 12. Light travels through this path and reaches the skin surface.

Figure 5:
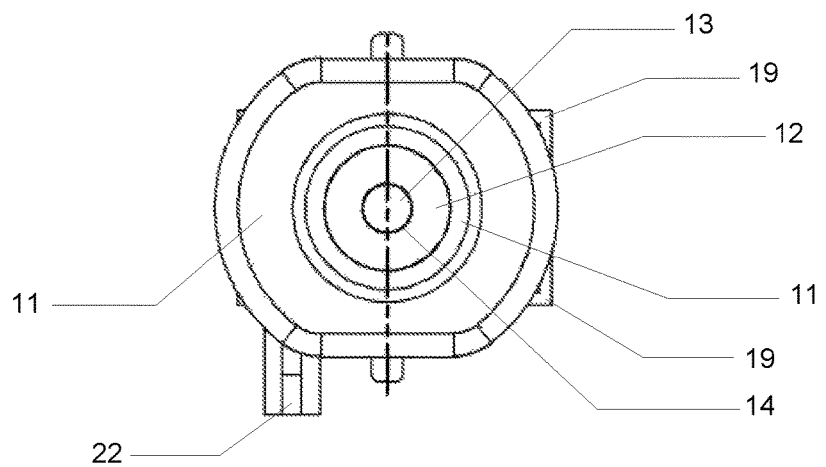
FIG. 5 shows the top view of optical apparatus

FIG. 5 shows the top view of the optical apparatus. This is a moving part inside the measurement device. When this apparatus applied on to the skin surface with a sufficient pressure, it moves inside the device and touches to a switch by a switch contact point 22. This contact activates the system and initiates the measurement.

What is claimed is:

1. An optical apparatus for obtaining a reflectance spectrum; comprising:
   a first means for generating a light,
   a second means for transferring and receiving the light on a substrate,
   a third means for collecting a diffusely reflected light, and
   a fourth means for separating the diffusely reflected light from a specular reflected light to obtain information about a concentration of a chromophore in the substrate;
   wherein the second means is an optic probe made of Poly(methyl methacrylate) (PMMA) material, the second means comprises an inner rod and an outer rod, the inner rod is nested within the outer rod for collection and for illumination, the inner rod and the outer rod are coaxial, the inner rod is longer than the outer rod, the inner rod is isolated from the outer rod with a semi mirrored isolator, the reflected light is reflected from deep within the substrate by the inner rod.

2. The optical apparatus according to claim 1, wherein the first means is two white LEDs, a flat spectrum of each of the two white LEDs has a wavelength ranging from 350 nm to 750 nm.

3. The optical apparatus according to claim 1, wherein the second means transfers the light to the substrate through the outer rod.

4. The optical apparatus according to claim 1, wherein the second means receives the light from the substrate through the inner rod.

5. The optical apparatus according to claim 1, wherein the third means detects a diffuse reflectance spectrum by a micro spectrometer.

6. The optical apparatus according to claim 1, wherein the fourth means separates the diffusely reflected light from the specular reflected light, the diffusely reflected light carries information about the presence or the concentration of the chromophore.

7. The optical apparatus according to claim 1, wherein
   a micro spectrometer is placed at an uppermost position of the optical apparatus,
   a LED light source is placed below the micro spectrometer directed to an optic probe,
   the optic probe is coupled to thee LED light source and the micro spectrometer to provide a compact structure.

* * * * *